United States Patent
Sakuma et al.

(10) Patent No.: US 11,827,797 B2
(45) Date of Patent: Nov. 28, 2023

(54) INK JET INK FOR TEXTILE PRINTING, INK SET, AND TEXTILE PRINTING METHOD

(71) Applicant: Seiko Epson Corporation, Tokyo (JP)

(72) Inventors: Daisuke Sakuma, Minowa (JP); Hiroaki Maruyama, Shiojiri (JP); Hidehiko Komatsu, Chino (JP)

(73) Assignee: SEIKO EPSON CORPORATION

( * ) Notice: Subject to any disclaimer, the term of this patent is extended or adjusted under 35 U.S.C. 154(b) by 1026 days.

(21) Appl. No.: 16/668,012

(22) Filed: Oct. 30, 2019

(65) Prior Publication Data

US 2020/0131390 A1    Apr. 30, 2020

(30) Foreign Application Priority Data

Oct. 31, 2018   (JP) ................. 2018-205055

(51) Int. Cl.
| | | |
|---|---|---|
| *C09D 11/328* | (2014.01) | |
| *C07D 253/075* | (2006.01) | |
| *C09D 11/38* | (2014.01) | |
| *C09D 4/00* | (2006.01) | |
| *C09D 5/00* | (2006.01) | |
| *C09D 11/00* | (2014.01) | |
| *B41J 3/407* | (2006.01) | |

(52) U.S. Cl.
CPC ........... *C09D 11/328* (2013.01); *B41J 3/4078* (2013.01); *C07D 253/075* (2013.01); *C09D 11/38* (2013.01)

(58) Field of Classification Search
CPC ........ C09D 11/328; C09D 11/38; C09D 4/00; C09D 5/00; C09D 11/00; B41J 3/4078; C07D 253/075
USPC ................................ 106/31.01, 31.13, 31.47
See application file for complete search history.

(56) References Cited

U.S. PATENT DOCUMENTS

| | | | |
|---|---|---|---|
| 9,909,024 B2* | 3/2018 | Komatsu | C09D 11/328 |
| 2005/0235867 A1 | 10/2005 | Jackson et al. | |
| 2007/0092703 A1* | 4/2007 | Leenders | C09D 4/00 428/195.1 |
| 2015/0166807 A1* | 6/2015 | Komatsu | C08K 5/21 347/20 |
| 2016/0257834 A1* | 9/2016 | Ito | C09D 17/001 |
| 2016/0298460 A1* | 10/2016 | Bryant | F01D 5/10 |

FOREIGN PATENT DOCUMENTS

| | | | |
|---|---|---|---|
| CN | 102108641 A | * | 6/2011 |
| CN | 105369652 A | | 3/2016 |
| EP | 2311917 A1 | | 4/2011 |
| JP | S61-266470 A | | 11/1986 |
| JP | S63-21991 A | | 1/1988 |
| JP | 2007-534802 A | | 11/2007 |
| WO | WO-2010-013649 A1 | | 2/2010 |

* cited by examiner

*Primary Examiner* — James E McDonough
(74) *Attorney, Agent, or Firm* — Harness, Dickey & Pierce, P.L.C.

(57) ABSTRACT

An ink jet ink for textile printing contains a reactive dye, where 1.2% by mass or more and 2.3% by mass or less of C.I. Reactive Blue 49 based on the total amount of the ink is contained as the reactive dye.

12 Claims, No Drawings

INK JET INK FOR TEXTILE PRINTING, INK SET, AND TEXTILE PRINTING METHOD

The present application is based on, and claims priority from, JP Application Serial Number 2018-205055, filed Oct. 31, 2018, the disclosure of which is hereby incorporated by reference herein in its entirety.

BACKGROUND

1. Technical Field

The present disclosure relates to an ink jet ink for textile printing, an ink set, and a textile printing method.

2. Related Art

An ink jet recording method is a method of recording by discharging ink droplets from fine nozzles and attaching the droplets to recording media. This method is characterized in that high-resolution high-grade images can be recorded at high speed by using relatively inexpensive apparatus. The ink jet recording method involves a great many factors to be considered, such as the properties of inks to be used, stability in recording, and the quality of obtained images. Not only ink jet recording apparatus, but also inks to be used are actively studied.

Moreover, the ink jet recording method is also applied to dyeing (printing) of fabrics or the like. Conventionally, textile screen printing, textile roller printing, and the like have been employed as printing methods for fabrics (woven fabrics and nonwoven fabrics). However, in view of efficiency in high-mix low-volume production, immediate printing properties, and the like, the ink jet recording method is advantageously employed and thus investigated variously.

For example, International Publication No. 2010/013649 discloses an ink composition, called a light ink, that enables high-lightness textile printing. In International Publication No. 2010/013649, a light ink is obtained by decreasing the concentration of a dye, compared with common inks.

The light ink disclosed in International Publication No. 2010/013649 is prepared by decreasing the concentration of a dye contained. However, when a dye that exhibits intense coloring properties is used, the concentration needs to be further decreased to achieve low optical density (OD) suitable for a light ink. Consequently, light resistance becomes insufficient in some cases. This problem tends to arise, in particular, in a light black (gray) ink. Accordingly, there is a need for an ink jet ink for textile printing that achieves both suitable optical density (OD) and high light resistance.

SUMMARY

An embodiment of an ink jet ink for textile printing according to the present disclosure is an ink jet ink for textile printing containing a reactive dye, where 1.2% by mass or more and 2.3% by mass or less of C.I. Reactive Blue 49 based on a total amount of the ink is contained as the reactive dye.

In an embodiment of the above-mentioned ink jet ink for textile printing, a total content of nickel ions, cobalt ions, and chromium ions in the ink may be 10.0 ppm or less based on the total amount of the ink.

In either embodiment of the above-mentioned ink jet inks for textile printing, a reactive dye having a maximum absorption wavelength of 500.0 nm or more and less than 550.0 nm; and a reactive dye having a maximum absorption wavelength of 400.0 nm or more and less than 500.0 nm may be further contained.

In any embodiment of the above-mentioned ink jet inks for textile printing, a content of the reactive dye having a maximum absorption wavelength of 400.0 nm or more and less than 500.0 nm may be 20.0 parts by mass or more and 30.0 parts by mass or less relative to 100 parts by mass of C.I. Reactive Blue 49 contained.

In any embodiment of the above-mentioned ink jet inks for textile printing, a content of the reactive dye having a maximum absorption wavelength of 500.0 nm or more and less than 550.0 nm may be 10.0 parts by mass or more and 20.0 parts by mass or less relative to 100 parts by mass of C.I. Reactive Blue 49 contained.

In any embodiment of the above-mentioned ink jet inks for textile printing, the reactive dye having a maximum absorption wavelength of 400.0 nm or more and less than 500.0 nm may have a structure represented by the following formula (I):

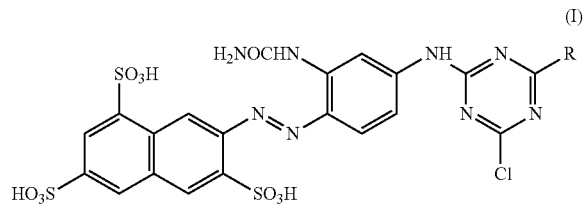

where R represents —NHCH$_2$CH$_2$SO$_3$H, —NH$_2$, or —CH$_2$CH$_2$OCH$_2$CH$_2$OH.

In any embodiment of the above-mentioned ink jet inks for textile printing, the reactive dye having a maximum absorption wavelength of 500.0 nm or more and less than 550.0 nm may have a structure represented by the following formula (II):

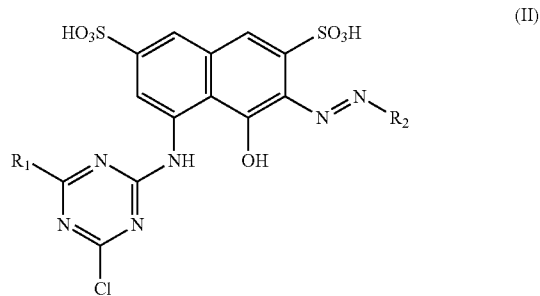

where R$^1$ is selected from groups represented by the following formula (III), formula (IV), formula (V), and formula (VI) (in each formula, a position represented by a dashed line is a connection point); and R$^2$ is selected from groups represented by the following formula (VII) and formula (VIII) (in each formula, a position represented by a dashed line is a connection point).

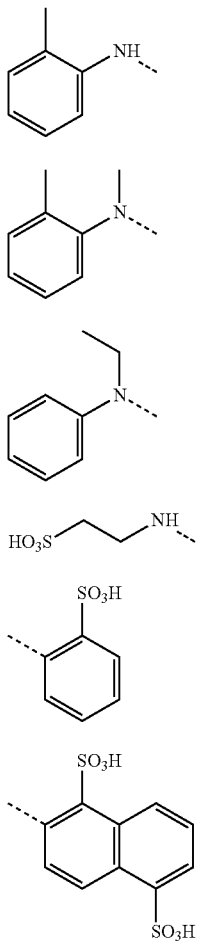

In any embodiment of the above-mentioned ink jet inks for textile printing, when a fabric is printed with the ink, a* may be −20.0 or more and 0.0 or less, b* may be −20.0 or more and 0.0 or less, and L* may be 30.0 or more and 80.0 or less.

In any embodiment of the above-mentioned ink jet inks for textile printing, C.I. Reactive Black 39 may be further contained, where a content of C.I. Reactive Black 39 may be 10.0 parts by mass or more and 25.0 parts by mass or less relative to 100 parts by mass of C.I. Reactive Blue 49 contained.

In any embodiment of the above-mentioned ink jet inks for textile printing, a content of a chelating agent may be 500.0 ppm or less based on the total amount of the ink.

An embodiment of an ink set according to the present disclosure includes any of the above-mentioned ink jet inks for textile printing.

In an embodiment of the above-mentioned ink set, all inks included in the ink set may have a total content of nickel ions, cobalt ions, and chromium ions of 10.0 ppm or less based on a total amount of each ink.

An embodiment of a textile printing method according to the present disclosure includes attaching any of the above-mentioned ink jet inks for textile printing to a recording medium.

DESCRIPTION OF EXEMPLARY EMBODIMENTS

Hereinafter, embodiments of the present disclosure will be described. The following embodiments will be described as examples of the present disclosure. Accordingly, the present disclosure is by no means limited to the following embodiments and includes various modifications carried out without changing the gist of the present disclosure. It is noted that all the constitution described hereinafter is not necessarily the essential constitution of the present disclosure.

1. Ink Jet Ink for Textile Printing

An ink jet ink for textile printing according to the embodiment contains a reactive dye and contains, as the reactive dye, 1.2% by mass or more and 2.3% by mass or less of C.I. Reactive Blue 49 based on a total amount of the ink.

1.1. Reactive Dyes

The ink jet ink for textile printing according to the embodiment contains a reactive dye. As the reactive dye, C.I. Reactive Blue 49 (hereinafter, also referred to as "Reactive Blue 49" or "RB 49" in some cases) is contained, and RB 49 is contained at 1.2% by mass or more and 2.3% by mass or less based on the total amount of the ink. The ink jet ink for textile printing according to the embodiment may contain reactive dyes other than RB 49, and such reactive dyes will be described hereinafter.

1.1.1. Reactive Blue 49

C.I. Reactive Blue 49 (RB 49) is a reactive dye of CAS No.: 12236-92-9 and chemical name: 1-amino-9,10-dihydro-9,10-dioxo-4-[[3-[[6-[(3-sufophenyl)amino]-4-chloro-1,3,5-triazin-2-yl]amino]-2,4,6-trimethyl-5-sufophenykl]amino]anthrathene-2-sulfonic acid.

RB 49 has satisfactory light resistance after being printed on fabrics. "Light resistance" herein represents resistance to light irradiation and indicates resistance to changes in optical density (OD) and/or hue before and after irradiation. Light resistance can be evaluated by the extent of optical density maintained before and after light irradiation. Moreover, light resistance can also be evaluated by the extent of changes in hue before and after light irradiation. According to the present disclosure, out of light resistance evaluated as mentioned above, at least light resistance that is evaluated by the extent of optical density (OD) maintained can be satisfactorily achieved. In addition, according to the present disclosure, light resistance that is evaluated by the extent of changes in hue can also be enhanced together in some cases.

Moreover, RB 49 does not contain any metal element within the structure and is thus environmentally friendly.

RB 49 is excellent in light resistance, but the coloring properties are inferior to other reactive dyes. Herein, "coloring properties" represent absorbance (Abs.) of light in the visible region. RB 49 has an Abs. of about 0.17 at a local maximum absorption wavelength λ1 of a solution in which the dye is diluted to 100 ppm. The measurement can be performed by using a V-770 UV-visible/NIR spectrophotometer (from JASCO Corporation).

When a dye species with a low Abs. per concentration is used, optical density (OD value) decreases compared with a dye species with a high Abs. per concentration in textile printing using these dyes at the same concentration. Accordingly, by using a dye species with a low Abs. per concentration, it is possible to readily achieve low optical density (OD), which is suitable for expressing a light color. The Abs. per 100 ppm dilution solution of a dye is preferably 0.19 or less and more preferably 0.18 or less.

When light-color textile printing is performed using other reactive dyes having higher coloring properties, the concentration needs to be lowered. In such a case, by using RB 49, the concentration of the reactive dye, in other words, RB 49 in an ink can be increased due to the low coloring properties of RB 49. Consequently, the concentration of a reactive dye can be increased in light-color textile printing, compared with a case in which a reactive dye having higher coloring properties is used. Accordingly, light resistance can be further enhanced while maintaining a desirable light color.

RB 49 can achieve both satisfactory light resistance and optical density (OD) by being included at 1.2% by mass or more and 2.3% by mass or less based on the total amount of an ink.

Moreover, by performing mixed-color textile printing using, as reactive dyes, RB 49 as a main component mixed with other reactive dyes, both satisfactory light resistance and optical density (OD) are readily achieved. In other words, by using RB 49 as a base and other reactive dyes for complementary colors, both light resistance and optical density (OD) can be achieved. Specifically, when used as a mixed color, color deviation can be reduced since RB 49 has excellent light resistance.

The ink jet ink for textile printing of the embodiment contains C.I. Reactive Blue 49 at 1.2% by mass or more and 2.3% by mass or less, more preferably 1.5% by mass or more and 2.2% by mass or less, and further preferably 1.7% by mass or more and 2.2% by mass or less based on the total amount of the ink. When the content of RB 49 falls within a more preferably range, both optical density (OD) and light resistance can be achieved further satisfactorily.

1.1.2. Other Reactive Dyes

The ink jet ink for textile printing of the embodiment may contain reactive dyes other than RB 49 as complementary colors. Examples of such reactive dyes include C.I. Reactive Yellow 2, 3, 6, 7, 12, 15, 17, 18, 22, 23, 24, 25, 27, 37, 39, 42, 57, 69, 76, 81, 84, 85, 86, 87, 92, 95, 102, 105, 111, 125, 135, 136, 137, 142, 143, 145, 151, 160, 161, 165, 167, 168, 175, 176, and 181; C.I. Reactive Red 2, 3, 3:1, 4, 5, 7, 8, 11, 12, 13, 15, 16, 21, 22, 23, 24, 24:1, 25, 26, 28, 29, 31, 32, 33, 35, 39, 40, 41, 43, 45, 46, 49, 55, 56, 58, 59, 65, 66, 78, 83, 106, 111, 112, 113, 114, 116, 120, 123, 124, 128, 130, 136, 141, 147, 158, 159, 171, 174, 176, 180, 183, 184, 187, 190, 193, 194, 195, 198, 218, 220, 222, 223, 226, 228, 235, and 245; C.I. Reactive Blue 2, 3, 4, 5, 7, 13, 14, 15, 19, 21, 25, 26, 27, 28, 29, 38, 39, 40, 41, 46, 50, 52, 63, 69, 71, 72, 77, 79, 89, 104, 109, 112, 113, 114, 116, 119, 120, 122, 137, 140, 143, 147, 160, 161, 162, 163, 168, 171, 176, 182, 184, 191, 194, 195, 198, 203, 204, 207, 209, 211, 214, 220, 221, 222, 231, 235, and 236; and C.I. Reactive Black 1, 2, 3, 5, 8, 10, 12, 13, 14, 31, 34, and 39.

Moreover, reactive dyes other than the above-described four basic colors, such as orange, violet, green, and brown, may also appropriately be used as complementary colors. Specific examples of such reactive dyes include C.I. Reactive Orange 1, 2, 4, 5, 7, 11, 12, 13, 15, 16, 20, 30, 35, 56, 64, 67, 69, 70, 72, 74, 82, 84, 86, 87, 91, 92, 93, 95, 99, and 107; C.I. Reactive Violet 1, 2, 4, 5, 6, 22, 23, 33, 36, and 38; C.I. Reactive Green 5, 8, 12, 15, 19, and 21; and C.I. Reactive Brown 1, 2, 7, 8, 9, 10, 11, 14, 17, 18, 19, 21, 23, 31, 37, 43, and 46.

One or two or more of these additionally and optionally included reactive dyes may be used. When the ink jet ink for textile printing of the embodiment contains the above-described reactive dyes as complementary colors, the total content is 0.1 part by mass or more and 50.0 parts by mass or less, preferably 0.5 part by mass or more and 45.0 parts by mass or less, more preferably 1.0 part by mass or more and 40.0 parts by mass or less, and further preferably 5.0 parts by mass or more and 30.0 parts by mass or less relative to 100 parts by mass of RB 49. When the total content falls within such ranges, it is possible to obtain desirable hue and to reduce changes in hue due to excellent light resistance of RB 49.

The above-illustrated reactive dyes used as complementary colors include metal element-containing dyes and metal element-free dyes. When used as complementary colors, metal element-free reactive dyes are more preferably selected. Consequently, environmental friendliness of the ink jet ink for textile printing can be readily achieved.

1.2. Complementary Colors and Hue

The ink jet ink for textile printing of the embodiment contains RB 49 and is suitable for light-color textile printing, as described above. Moreover, when the color of a fabric to be printed is light black (gray) having a* of −20.0 or more and 0.0 or less, b* of −20.0 or more and 0.0 or less, and L* of 30.0 or more and 80.0 or less in the CIELAB color space, the ink jet ink for textile printing of the embodiment can perform textile printing with further excellent optical density (OD) and light resistance by using predetermined reactive dyes below as complementary colors, compared with textile printing using black reactive dyes.

Specifically, when light black (gray) textile printing is performed by using black reactive dyes having high coloring properties, the concentration of these dyes in an ink needs to be lowered. However, by using RB 49, the concentration of the reactive dye, in other words, RB 49 can be increased. Consequently, light resistance can be further enhanced compared with a case of using black reactive dyes having high coloring properties.

When the color of a fabric to be printed is light black (gray) having a* of −20.0 or more and 0.0 or less, b* of −20.0 or more and 0.0 or less, and L* of 30.0 or more and 80.0 or less in the CIELAB color space, reactive dyes to be used as complementary colors may be appropriately selected from the above-described other reactive dyes. It is preferable to include a reactive dye having a maximum absorption wavelength of 500.0 nm or more and less than 550.0 nm and a reactive dye having a maximum absorption wavelength of 400.0 nm or more and less than 500.0 nm. A plurality of reactive dyes having these absorption wavelength characteristics may be used as the respective reactive dyes.

By including two types of reactive dyes having maximum absorption wavelengths within the above-mentioned ranges, the color of a fabric to be printed easily satisfies a* of −20.0 or more and 0.0 or less, b* of −20.0 or more and 0.0 or less, and L* of 30.0 or more and 80.0 or less in the CIELAB color space.

Examples of the reactive dye having a maximum absorption wavelength of 500.0 nm or more and less than 550.0 nm include C.I. Reactive Red 3:1, 24, 24:1, 31, 226, and 245.

Further, examples of the reactive dye having a maximum absorption wavelength of 400.0 nm or more and less than 500.0 nm include C.I. Reactive Yellow 95 and 181; and C.I. Reactive Orange 12, 13, and 99.

When the reactive dye having a maximum absorption wavelength of 400.0 nm or more and less than 500.0 nm is included in the ink jet ink for textile printing of the embodiment, the content is more preferably 20.0 parts by mass or more and 30.0 parts by mass or less relative to 100 parts by mass of RB 49. At this content, the color of a fabric to be printed readily satisfies a* of −20.0 or more and 0.0 or less, b* of −20.0 or more and 0.0 or less, and L* of 30.0 or more and 80.0 or less in the CIELAB color space.

When the reactive dye having a maximum absorption wavelength of 500.0 nm or more and less than 550.0 nm is included in the ink jet ink for textile printing of the embodiment, the content is more preferably 10.0 parts by mass or more and 20.0 parts by mass or less relative to 100 parts by mass of RB 49. At this content, the color of a fabric to be printed readily satisfies a* of −20.0 or more and 0.0 or less, b* of −20.0 or more and 0.0 or less, and L* of 30.0 or more and 80.0 or less in the CIELAB color space.

Moreover, when the reactive dye having a maximum absorption wavelength of 400.0 nm or more and less than 500.0 nm is included in the ink jet ink for textile printing of the embodiment, at least one of reactive dyes having a structure represented by formula (I) below is more preferably used. Any of the reactive dyes having the structure represented by formula (I) has a maximum absorption wavelength of 400.0 nm or more and less than 500.0 nm.

The reactive dyes having the structure represented by formula (I) below exhibit light resistance comparable to RB 49. When a dye used as a complementary color has light resistance different from RB 49, the hue of recorded articles changes over long-term exposure to light in some cases. However, it is possible to suitably reduce changes in hue of recorded articles when the reactive dyes having the structure represented by formula (I) below exhibit light resistance comparable to RB 49. Changes in hue herein can be evaluated by determining a color difference ($\Delta E^*$) before and after a light resistance test, and the color difference ($\Delta E^*$) can be estimated on the basis of the following numerical formulae 2 to 5;

$$\Delta E^* = [(\Delta L^*)^2 + (\Delta a^*)^2 + (\Delta b^*)^2]^{1/2} \quad (2)$$

$$\Delta L^* = L^*_1 - L^*_2 \quad (3)$$

$$\Delta a^* = a^*_1 - a^*_2 \quad (4)$$

$$\Delta b^* = b^*_1 - b^*_2 \quad (5)$$

where $L^*_1$, $a^*_1$, and $b^*_1$ represent initial L*, a*, and b* values of a printed fabric, respectively, and $L^*_2$, $a^*_2$, and $b^*_2$ represent L*, a*, and b* values after a light resistance test, respectively:

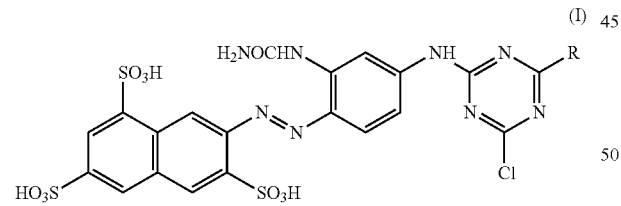

where R represents —NHCH$_2$CH$_2$SO$_3$H, —NH$_2$, or —CH$_2$CH$_2$OCH$_2$CH$_2$OH.

The names of the reactive dyes represented by formula (I) are C.I. Reactive Orange 99 when R is —NHCH$_2$CH$_2$SO$_3$H, C.I. Reactive Orange 12 when R is —NH$_2$, and C.I. Reactive Yellow 181 when R is —CH$_2$CH$_2$OCH$_2$CH$_2$OH.

When the reactive dye having a maximum absorption wavelength of 500.0 nm or more and less than 550.0 nm is included in the ink jet ink for textile printing of the embodiment, at least one of reactive dyes having a structure represented by formula (II) below are more preferably used. Any of the reactive dyes having the structure represented by formula (II) has a maximum absorption wavelength of 500.0 nm or more and less than 550.0 nm.

The reactive dyes having the structure represented by formula (II) below have light resistance comparable to RB 49. When a dye used as a complementary color has light resistance different from RB 49, the hue of recorded articles changes over long-term exposure to light in some cases. However, it is possible to suitably reduce changes in hue of recorded articles when the reactive dyes having the structure represented by formula (II) below exhibit light resistance comparable to RB 49:

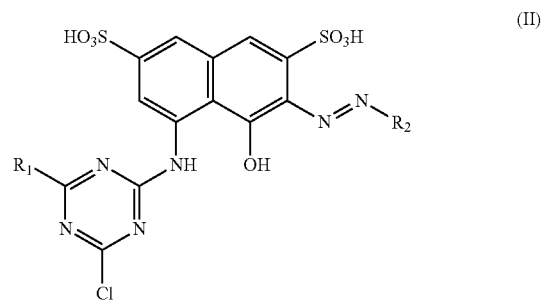

where $R^1$ is selected from groups represented by the following formula (III), formula (IV), formula (V), and formula (VI) (in each formula, a position represented by a dashed line is a connection point); and $R^2$ is selected from groups represented by the following formula (VII) and formula (VIII) (in each formula, a position represented by a dashed line is a connection point).

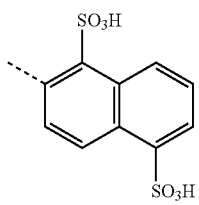
(VIII)

Some of the names of the reactive dyes represented by formula (II) are C.I. Reactive Red 3:1 when $R^1$ is formula (III) and $R^2$ is formula (VII), C.I. Reactive Red 24 when $R^1$ is formula (IV) and $R^2$ is formula (VII), C.I. Reactive Red 24:1 when $R^1$ is formula (V) and $R^2$ is formula (VII), C.I. Reactive Red 226 when $R^1$ is formula (VI) and $R^2$ is formula (VII), and C.I. Reactive Red 245 when $R^1$ is formula (V) and $R^2$ is formula (VIII).

The ink jet ink for textile printing of the embodiment may contain reactive dyes appropriately selected from the above-described other reactive dyes as complementary colors. Moreover, the ink may also contain C.I. Reactive Black 39 (hereinafter, also referred to as "RBk 39" in some cases) as a complementary color.

C.I. Reactive Black 39 (RBk 39) is a reactive dye of a chemical name: 4-amino-6-[[5-[(4-amino-6-chloro-1,3,5-triazin-2-yl)amino]-2-(sodiooxysulfonyl)phenyl]azo]-3-[[2,5-bis(sodiooxysulfonyl)phenyl]azo]-5-hydroxy-2,7-naphthalenedisulfonic acid disodium salt.

RBk 39 is a black reactive dye as well as an azo dye and has an Abs. (when diluted to 100 ppm) of 0.41. By using RBk 39, satisfactory chlorine resistance of printed articles can be achieved. This is presumably because decomposition by chlorine is less likely to proceed since RBk 39 is an azo dye and lacks a quinoxaline skeleton. In the embodiment, chlorine resistance represents resistance of printed articles to exposure to chlorine and can be evaluated by the extent of optical density (OD) maintained and/or the extent of changes in hue.

Meanwhile, RBk 39 is an azo dye and is inferior in light resistance to RB 49 having a quinoxaline skeleton. In other words, when only RBk 39, which is readily susceptible to decomposition by light, is used, the OD value of a printed article is considerably lowered over time.

Moreover, RBk 39 has an Abs. of 0.41 (when diluted to 100 ppm), which is higher than an Abs. of 0.17 for RB 49 (when diluted to 100 ppm). Accordingly, when RBk 39 and RB 49 are printed on textile at the same concentration, the OD value of RBk 39 is higher than that of RB 49. This means that the concentration of RBk 39 needs to be lowered compared with RB 49 to express a color tone with a low OD value (gray color, for example). In view of this, too, satisfactory light resistance is difficult to be achieved by using RBk 39 alone.

Meanwhile, by using RB 49 as a base and RBk 39 as a complementary color, it is possible to achieve both excellent performance of these dyes.

When RBk 39 is included as a complementary color in the ink jet ink for textile printing of the embodiment, the content is preferably 10.0 parts by mass or more and 25.0 parts by mass or less relative to 100 parts by mass of RB 49. By controlling the content within this range, textile printing with excellent chlorine resistance and light resistance is readily performed.

1.3. Other Components

The ink jet ink for textile printing of the embodiment may contain an organic solvent, water, a chelating agent, and/or other substances.

1.3.1. Organic Solvents

The ink jet ink for textile printing of the embodiment may contain an organic solvent. Examples of the organic solvent include cyclic amides, alkylpolyols, glycol ethers, and other organic solvents.

1.3.1.1. Cyclic Amides

The ink jet ink for textile printing of the embodiment may contain a cyclic amide. Such cyclic amides readily dissolve the above-described dyes and act to suppress solidification or drying of the ink jet ink for textile printing.

Examples of the cyclic amides include compounds having an amide group-containing ring structure and specifically, compounds represented by the following formula (A):

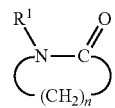

where: $R^1$ is hydrogen or an alkyl group having 1 to 4 carbon atoms; n is an integer of 1 to 7; and the alkyl group may be linear or branched.

Examples of the compounds represented by formula (A) include γ-lactams, such as 2-pyrrolidone, 1-methyl-2-pyrrolidone (N-methyl-2-pyrrolidone), 1-ethyl-2-pyrrolidone (N-ethyl-2-pyrrolidone), N-vinyl-2-pyrrolidone, 1-propyl-2-pyrrolidone, 1-butyl-2-pyrrolidone; β-lactams; δ-lactams; and ε-lactams, such as ε-caprolactam. The numerical values in the brackets each represent a normal boiling point. These cyclic amides may be used alone or in combination.

When cyclic amides are used, the total content is 1% by mass or more and 30% by mass or less, preferably 3% by mass or more and 30% by mass or less, more preferably 3% by mass or more and 20% by mass or less, and further preferably 3% by mass or more and 10% by mass or less, based on the total mass of the ink jet ink for textile printing.

When the total content of cyclic amides falls within the above-mentioned ranges, the solubility of reactive dyes to be contained, for example, can be enhanced in some cases. In such a case, the amount (concentration) of reactive dyes to be included can be increased.

1.3.1.2. Alkylpolyols

The ink jet ink for textile printing of the embodiment may contain an alkylpolyol. By including an alkylpolyol, it is possible to further enhance moisture retention properties of the ink jet ink for textile printing, ensure excellent discharge stability by an ink jet method, and effectively suppress moisture evaporation from a recording head during the long-term unused state. Moreover, by including an alkylpolyol, it is possible to maintain satisfactory stability in continuous discharge and/or recovery properties from the unused state even when a type of dye that tends to cause clogging of a nozzle is used.

Specific examples of the alkylpolyols include 1,2-butanediol, 1,2-pentanediol, 1,2-hexanediol, 1,2-heptanediol, 1,3-propanediol, 1,3-butanediol, 1,4-butanediol, 1,5-pentanediol, 1,6-hexanediol, 2-ethyl-2-methyl-1,3-propanediol, 2-methyl-2-propyl-1,3-propanediol, 2-methyl-1,3-propanediol, 2,2-dimethyl-1,3-propanediol, 3-methyl-1,3-butanediol, 2-ethyl-1,3-hexanediol, 3-methyl-1,5-pentanediol, 2-methylpentane-2,4-diol, diethylene glycol, propylene glycol, and dipropylene glycol. These alkylpolyols may be used alone or in combination.

When an alkylpolyol is included, the effect can be exerted at the content of 5% by mass or more based on the total mass of the ink jet ink for textile printing. The content is preferably 5% by mass or more and 40% by mass or less, more preferably 10% by mass or more and 30% by mass or less, and further preferably 15% by mass or more and 25% by mass or less.

The ink jet ink for textile printing of the embodiment preferably does not contain any alkylpolyol having a normal boiling point of 260° C. or higher. This is because an alkylpolyol having a normal boiling point of 260° C. or higher tends to interfere dyeing, thereby causing deterioration in coloring properties and/or color reproducibility of images. Specific examples of the alkylpolyol having a normal boiling point of 260° C. or higher include triethylene glycol [287° C.] and glycerol [290° C.]

The wording "do/does not contain" in this specification will be described. For example, when the expression "do/does not contain A" means not only that A is not contained at all, but also that A is not included intentionally during manufacture of a composition. Accordingly, a trace amount of A incidentally included or generated during manufacture or storage of the composition may be contained. The wording "do/does not contain" specifically means "do/does not contain, for example, 1.0% by mass or more, preferably 0.5% by mass or more, more preferably 0.1% by mass or more, further preferably 0.05% by mass or more, and particularly preferably 0.01% by mass or more".

The foregoing "does not contain any alkylpolyol having a normal boiling point of 260° C. or higher" means "does not contain 1.0% by mass or more, preferably 0.5% by mass or more, more preferably 0.1% by mass or more, further preferably 0.05% by mass or more, and particularly preferably 0.01% by mass or more".

1.3.1.3. Glycol Ethers

The ink jet ink for textile printing of the embodiment may contain a glycol ether. Such glycol ethers are preferably monoalkyl ethers of glycols selected from ethylene glycol, diethylene glycol, triethylene glycol, polyethylene glycol, propylene glycol, dipropylene glycol, tripropylene glycol, polypropylene glycol, and polyoxyethylene-polyoxypropylene glycol. More preferable examples include methyl triglycol (triethylene glycol monomethyl ether), butyl triglycol (triethylene glycol monobutyl ether), butyl diglycol (diethylene glycol monobutyl ether), and dipropylene glycol monopropyl ether. Typical examples include diethylene glycol monobutyl ether.

A plurality of glycol ethers may be mixed and used. When glycol ethers are used, the total amount to be contained is 0.5% by mass or more and 30% by mass or less, preferably 1.0% by mass or more and 20% by mass or less, and more preferably 3.0% by mass or more and 10.0% by mass or less based on the total amount of the ink jet ink for textile printing, from a viewpoint of adjusting the viscosity of the ink jet ink for textile printing and preventing clogging through the moistening effect.

1.3.1.4. Other Organic Solvents

The ink jet ink for textile printing of the embodiment may contain other organic solvents. Examples of other solvents include lactones, such as γ-butyrolactone; and betaine compounds.

1.3.2. Water

The ink jet ink for textile printing of the embodiment may contain water. Exemplary water includes water from which ionic impurities have been removed as much as possible. Examples include pure water, such as deionized water, ultrafiltration water, reverse osmosis water, and distilled water; as well as ultrapure water. Moreover, by using water that has been sterilized, for example, by UV irradiation or addition of hydrogen peroxide, it is possible to suppress growth of bacteria and/or fungi during long-term storage of the ink jet ink for textile printing.

The water content is 30% by mass or more, preferably 40% by mass or more, more preferably 45% by mass or more, and further preferably 50% by mass or more, based on the total amount of the ink jet ink for textile printing. When the water content is 30% by mass or more, a relatively low viscosity of the ink jet ink for textile printing can be achieved. Moreover, the upper limit of the water content is preferably 90% by mass or less, more preferably 85% by mass or less, and further preferably 80% by mass or less, based on the total amount of the ink jet ink for textile printing.

1.3.3. Chelating Agents

The ink jet ink for textile printing of the embodiment may contain a chelating agent to remove unnecessary ions in the ink.

Examples of the chelating agents include ethylenediaminetetraacetic acid and its salts, such as EDTA, EDTA-2Na (ethylenediaminetetraacetic acid disodium salt), EDTA-3Na (ethylenediaminetetraacetic acid trisodium salt), EDTA-4Na (ethylenediaminetetraacetic acid tetrasodium salt), and EDTA-3K (ethylenediaminetetraacetic acid tripotassium salt); diethylenetriaminepentaacetic acid and its salts, such as DTPA, DTPA-2Na (diethylenetriaminepentaacetic acid disodium salt), and DTPA-5Na (diethylenetriaminepentaacetic acid pentasodium salt); nitrilotriacetic acid and its salts, such as NTA, NTA-2Na (nitrilotriacetic acid disodium salt), and NTA-3Na (nitrilotriacetic acid trisodium salt); ethylenediamine-N,N'-disuccinic acid and its salts; 3-hydroxy-2,2'-iminodisuccinic acid and its salts; L-aspartic acid-N,N-diacetic acid and its salts; and N-(2-hydroxyethyl) iminodiacetic acid and its salts.

Exemplary chelating agents other than acetic acid analogues include ethylenediaminetetra(methylenephosphonic acid) and its salts; ethylenediaminetetra(metaphosphoric acid) and its salts; ethylenediaminepyrophosphoric acid and its salts; and ethylenediaminemetaphosphoric acid and its salts.

When the ink jet ink for textile printing of the embodiment contains a chelating agent, one or two or more selected from the above-illustrated chelating agents may be used.

Among the above-illustrated chelating agents, exemplary chelating agents that exhibit satisfactory biodegradability and satisfactory environmental friendliness include ethylenediamine-N,N'-disuccinic acid and its salts; 3-hydroxy-2,2'-iminodisuccinic acid and its salts; L-aspartic acid-N,N-diacetic acid and its salts; and N-(2-hydroxyethyl) iminodiacetic acid and its salts.

When a chelating agent is included in the ink jet ink for textile printing of the embodiment, one or two or more selected from the above-mentioned chelating agents that exhibit satisfactory biodegradability are preferably used. Consequently, satisfactory environmental friendliness of the ink jet ink for textile printing can be achieved. In such a case, the content of a chelating agent is not particularly limited but is 2000.0 ppm or less, preferably 1000.0 ppm or less, more preferably 800.0 ppm or less, and further preferably 600.0 ppm or less, based on the total amount of the ink.

Meanwhile, when chelating agents with poor biodegradability or without biodegradability are included in the ink jet ink for textile printing of the embodiment, the total content is 500.0 ppm or less, preferably 400.0 ppm or less, more preferably 300.0 ppm or less, and further preferably 200.0 ppm or less, based on the total amount of the ink. When the content of chelating agents with poor biodegradability or without biodegradability is 500.0 ppm or less based on the total amount of the ink, it is possible to avoid considerable deterioration in environmental friendliness of the ink jet ink for textile printing.

1.3.4. Other Substances

The ink jet ink for textile printing of the embodiment may contain, as substances other than the above-described ones, surfactants, pH adjusters, preservatives, fungicides, urea derivatives, saccharides, and the like.

1.3.4.1. Surfactants

The ink jet ink for textile printing of the embodiment may contain a surfactant. Surfactants may be used for lowering surface tension of the ink jet ink for textile printing, thereby adjusting or enhancing wettability of recording media, such as permeability into fabrics and the like. For such surfactants, any of nonionic surfactants, anionic surfactants, cationic surfactants, and amphoteric surfactants may be used. Moreover, these surfactants may be used in combination. Among these surfactants, acetylenic glycol surfactants, silicone surfactants, and fluorosurfactants are preferably used.

Examples of the acetylenic glycol surfactants include, but are not particularly limited to, Surfynol 104, 104E, 104H, 104A, 104BC, 104DPM, 104PA, 104PG-50, 104S, 420, 440, 465, 485, SE, SE-F, 504, 61, DF37, CT111, CT121, CT131, CT136, TG, GA, and DF110D (trade names from Air Products and Chemicals Inc.); Olfine B, Y, P, A, STG, SPC, E1004, E1010, PD-001, PD-002W, PD-003, PD-004, PD-005, EXP. 4001, EXP. 4036, EXP. 4051, AF-103, AF-104, AK-02, SK-14, and AE-3 (trade names from Nissin Chemical Industry Co. Ltd.); and Acetylenol E00, E00P, E40, and E100 (trade names from Kawaken Fine Chemicals Co., Ltd.).

The silicone surfactants are not particularly limited and are preferably polysiloxane compounds, for example. Such polysiloxane compounds are not particularly limited and are polyether-modified organosiloxanes, for example. Exemplary commercial products of such polyether-modified organosiloxanes include BYK-306, BYK-307, BYK-333, BYK-341, BYK-345, BYK-346, and BYK-348 (trade names from BYK Japan KK); KF-351A, KF-352A, KF-353, KF-354L, KF-355A, KF-615A, KF-945, KF-640, KF-642, KF-643, KF-6020, X-22-4515, KF-6011, KF-6012, KF-6015, and KF-6017 (trade names from Shin-Etsu Chemical Co., Ltd.).

As the fluorosurfactants, fluorine-modified polymers are preferably used, and specific examples include BYK-340 (trade name from BYK Japan KK).

When surfactants are included in the ink jet ink for textile printing, the total content of the surfactants is 0.01% by mass or more and 3% by mass or less, preferably 0.05% by mass or more and 2% by mass or less, further preferably 0.1% by mass or more and 1.5% by mass or less, and particularly preferably 0.2% by mass or more and 1% by mass or less, based on the entire ink jet ink for textile printing.

Moreover, by including a surfactant in the ink jet ink for textile printing, stability tends to increase during discharge of the ink from a head.

1.3.4.2. pH Adjusters

The ink jet ink for textile printing of the embodiment may contain a pH adjuster. Such pH adjusters are not particularly limited, and examples include appropriate combinations of an acid, a base, a weak acid, and/or a weak base. Examples of acids and bases used for such combinations include inorganic acids, such as sulfuric acid, hydrochloric acid, and nitric acid; inorganic bases, such as lithium hydroxide, sodium hydroxide, potassium hydroxide, monopotassium phosphate, disodium phosphate, potassium carbonate, sodium carbonate, sodium bicarbonate, and ammonia; organic bases, such as triethanolamine, diethanolamine, monoethanolamine, tripropanolamine, triisopropanolamine, diisopropanolamine, and tris(hydroxymethyl)aminomethane (THAM); organic acids, such as adipic acid, citric acid, succinic acid, and lactic acid; Good's buffers, such as N,N-bis(2-hydroxyethyl)-2-aminoethanesulfonic acid (BES), 2-[4-(2-hydroxyethyl)-1-piperazinyl]ethanesulfonic acid (HEPES), 2-morpholinoethanesulfonic acid (MES), N-(carbamoylmethyl)iminodiacetic acid (ADA), piperazine-1,4-bis(2-ethanesulfonic acid) (PIPES), N-(2-acetamido)-2-aminoethanesulfonic acid (ACES), cholamine chloride hydrochloride, N-tris(hydroxymethyl)methyl-2-aminoethanesulfonic acid (TES), acetamidoglycine, tricine, glycinamide, and bicine; phosphate buffers; citrate buffers; and Tris buffers. Among these pH adjusters, pH adjusters preferably include, partially or exclusively, a tertiary amine, such as triethanolamine or triisopropanolamine; and a carboxy group-containing organic acid, such as adipic acid, citric acid, succinic acid, or lactic acid since pH buffering effects can be obtained in a further stable manner.

1.3.4.3. Preservatives, Fungicides, Corrosion Inhibitors

The ink jet ink for textile printing may contain a preservative and/or a fungicide. Examples of the preservative and the fungicide include sodium benzoate, pentachlorophenol sodium salt, 2-pyridinethiol 1-oxide sodium salt, sodium sorbate, sodium dehydroacetate, 1,2-benzisothiazolin-3-one (Proxel CRL, Proxel BDN, Proxel GXL, Proxel XL-2, Proxel TN, Proxel LV from Zeneca), and 4-chloro-3-methylphenol (Preventor CMK and so forth from Bayer AG).

Examples of the corrosion inhibitors include benzotriazole.

1.3.4.4. Urea Derivatives

The ink jet ink for textile printing may contain a urea derivative as a humectant or a dyeing aid for enhancing dyeing properties of dyes. Specific examples of the urea derivative include urea, ethyleneurea, tetramethylurea, thiourea, and 1,3-dimethyl-2-imidazolidinone. The content of the urea derivative, if contained, may be 1% by mass or more and 10% by mass or less based on the total mass of the ink jet ink for textile printing.

1.3.4.5. Saccharides

Saccharides may be used to suppress solidification or drying of the ink jet ink for textile printing. Specific examples of the saccharides include glucose, mannose, fructose, ribose, xylose, arabinose, galactose, aldonic acids, glucitol (sorbit), maltose, cellobiose, lactose, sucrose, trehalose, and maltotriose.

1.3.4.6. Others

As components other than the above-described ones, additives commonly and optionally used in ink jet inks for textile printing, such as antioxidants, UV absorbers, oxygen absorbers, and dissolution aids, may also be contained.

1.4. Metal and Metal Ion Content in Inks

The ink jet ink for textile printing of the embodiment more preferably has a low content of metal elements and their ions. The ink jet ink for textile printing of the embodiment preferably has a total content of nickel ions, cobalt ions, and chromium ions in the ink of 10.0 ppm or less based on the total amount of the ink. When the total content of these ions is 10 ppm or less, it is possible to avoid considerable deterioration in environmental friendliness of the ink jet ink for textile printing.

By using metal-containing reactive dyes in the ink jet ink for textile printing, the content of metal elements or their ions increases. As in the foregoing, however, RB 49 does not contain any metal. Accordingly, when reactive dyes as complementary colors are used, it is possible to reduce the content of metal elements and their ions in the ink jet ink for textile printing by using metal-free reactive dyes or by using a small amount of metal-containing reactive dyes.

The content of metal elements and their ions in the ink jet ink for textile printing can be measured by an ICP-MS (inductively coupled plasma-mass spectrometer) or an atomic absorption spectrometer, for example.

1.5. Manufacture and Physical Properties of Ink Jet Inks for Textile Printing

The ink jet ink for textile printing of the embodiment is obtained by mixing the components in an optional order and, as necessary, by removing impurities through filtration and the like. As the mixing method for the components, a method of successively adding materials to a vessel equipped with a stirring device, such as a mechanical stirrer or a magnetic stirrer, and mixing with stirring is suitably employed.

The ink jet ink for textile printing of the embodiment has a surface tension of preferably 20.0 mN/m or more and 40.0 mN/m or less and more preferably 22.0 mN/m or more and 35.0 mN/m or less in view of balanced textile printing quality and reliability as an ink jet ink for textile printing. Moreover, from the same viewpoint, the ink jet ink for textile printing has a viscosity at 20° C. of preferably 1.5 mPa·s or higher and 10.0 mPa·s or lower and more preferably 2.0 mPa·s or higher and 8.0 mPa·s or lower. To control the surface tension and viscosity within the above-mentioned ranges, types of the above-described solvents and/or surfactants as well as the amounts of these solvents, surfactants, and water to be added may be adjusted appropriately.

1.5. Ink Jet Method

The ink jet ink for textile printing of the embodiment is used for an ink jet method. According to the ink jet method, predetermined images can be formed by discharging the ink jet ink for textile printing from an ink jet head onto recording media, such as fabrics.

Exemplary ink jet modes include a mode of applying mechanical energy to inks by electrostrictive elements and a mode of applying thermal energy to inks. In the embodiment, the mode of applying mechanical energy to inks by electrostrictive elements is more preferably employed.

2. Ink Sets

The ink jet ink for textile printing of the embodiment can constitute an ink set through combination with other ink jet inks for textile printing containing optional-color dyes and with a pretreatment composition described hereinafter in any number of inks, in any number of pretreatment compositions, and in any number of colors.

According to the ink set of the embodiment, due to the ink jet ink for textile printing of the embodiment, it is possible to form images excellent in optical density (OD) and light resistance as well as remarkably suppress changes in hue (light resistance) of the images over time.

Further, all the inks included in the ink set of the embodiment are preferably selected from inks having the total content of nickel ions, cobalt ions, and chromium ions of 10.0 ppm or less based on the total amount of each ink. As this result, excellent environmental friendliness of the ink set can be achieved.

3. Textile Printing Method

A textile printing method of the embodiment includes attaching the above-described ink jet ink for textile printing to a recording medium (hereinafter, also referred to as "attaching step"). Hereinafter, recording media used for the textile printing method of the embodiment as well as the step and optional steps included in the textile printing method will be described.

3.1. Recording Media

The ink jet ink for textile printing of the embodiment is used by being attached onto a recording medium. Such recording media are not particularly limited, and examples include various fabrics. Examples of component materials for such fabrics include, but are not particularly limited to, natural fibers, such as cotton, hemp, wool, and silk; synthetic fibers, such as polypropylene, polyesters, acetate, triacetate, polyamides, and polyurethanes; biodegradable fibers, such as polylactic acid; and blended fibers thereof. The fabrics may be in any form of the above-mentioned fibers, such as woven fabrics, knitted fabrics, and nonwoven fabrics. Fabrics to be used in the embodiment are more preferably formed from cellulose-containing fibers, such as cotton and hemp, among the above-mentioned component materials. By using these fabrics, further excellent dyeing properties of the ink jet ink for textile printing can be achieved.

The weight of a fabric to be used in the embodiment is in the range of 1.0 oz (ounce) or more and 10.0 oz or less, preferably 2.0 oz or more and 9.0 oz or less, more preferably 3.0 oz or more and 8.0 oz or less, and further preferably 4.0 oz or more and 7.0 oz or less.

3.2. Pretreatment Step

The textile printing method of the embodiment may include a pretreatment step of applying to a fabric a pretreatment composition that contains at least one of an alkaline agent, an acid, and a hydrotropic agent. Through this step, dyeing properties of dyes are further enhanced.

Exemplary methods of applying a pretreatment composition include a method of immersing a fabric in a pretreatment composition, a method of applying a pretreatment composition with a roll coater or the like, and a method of spraying a pretreatment composition (ink jet method or spraying method, for example). Any of these methods can be employed.

Pretreatment Compositions

A pretreatment composition contains at least one of an alkaline agent, an acid, and a hydrotropic agent. The contents of these components in the pretreatment composition are not particularly limited and may be appropriately determined corresponding to the types of fabrics, for example.

When reactive dyes are used, an alkaline agent is preferably used from a viewpoint of further enhancing dyeing properties of the reactive dyes. Specific examples of the alkaline agent include sodium carbonate, sodium bicarbonate, sodium hydroxide, trisodium phosphate, and sodium acetate.

When acid dyes are used, an acid is preferably used from a viewpoint of further enhancing dyeing properties of the acid dyes. As specific examples of the acid, organic acids, such as carboxylic acids having a carboxy group within the molecule and sulfonic acids having a sulfo group within the molecule; or ammonium salts of strong acids are widely used. Among these acids, ammonium sulfate is particularly preferable.

The hydrotropic agent is preferably used from a viewpoint of enhancing coloring properties of recorded images. Exemplary hydrotropic agents include the urea derivatives illustrated in the foregoing section on the ink jet ink for textile printing.

The pretreatment composition of the embodiment may contain water. Such water is the same as water described concerning the foregoing ink jet ink for textile printing. The content of water is 30% by mass or more, preferably 40% by mass or more, more preferably 45% by mass or more, and further preferably 50% by mass or more, based on the total amount of the pretreatment composition.

The pretreatment composition of the embodiment may contain a water-soluble organic solvent. Such water-soluble organic solvents can enhance wettability of recording media with the pretreatment composition in some cases. Exemplary water-soluble organic solvents include at least one of esters, alkylene glycol ethers, cyclic esters, and alkoxylkylamides. Moreover, water-soluble organic solvents may be nitrogen-containing compounds, saccharides, amines, and the like other than the above-mentioned exemplary solvents. Further, the pretreatment composition may contain water-soluble organic solvents that may be used for the foregoing ink jet ink for textile printing.

The pretreatment composition may contain a plurality of water-soluble organic solvents. When water-soluble organic solvents are contained, the total content of the water-soluble organic solvents is 0.1% by mass or more and 20% by mass or less, preferably 0.3% by mass or more and 15% by mass or less, more preferably 0.5% by mass or more and 10% by mass or less, and further preferably 1% by mass or more and 7% by mass or less, based on the entire pretreatment composition.

A pretreatment composition may contain a sizing agent. Exemplary sizing agents include starch substances, such as corn and wheat; cellulosic substances, such as carboxymethyl cellulose and hydroxymethyl cellulose; polysaccharides, such as sodium alginate, gum arabic, locust bean gum, tragacanth gum, guar gum, and tamarind seed; proteins, such as gelatin and casein; natural water-soluble polymers, such as tannins and lignin; and synthetic water-soluble polymers, such as polyvinyl alcohol-based compounds, polyethylene oxide-based compounds, acrylic acid-based compounds, and maleic anhydride-based compounds.

The pretreatment composition may contain a surfactant. Such surfactants are the same as those described for the foregoing ink jet ink for textile printing. When the pretreatment composition contains surfactants, the total surfactant content is 0.01% by mass or more and 3% by mass or less, preferably 0.05% by mass or more and 2% by mass or less, further preferably 0.1% by mass or more and 1% by mass or less, and particularly preferably 0.2% by mass or more and 0.5% by mass or less, based on the entire pretreatment composition.

By including a surfactant in the pretreatment composition, it is possible to control wettability and permeability of inks applied onto pretreated fabrics, thereby realizing suppressed bleeding and enhanced coloring properties of printed articles.

The pretreatment composition of the embodiment may contain components commonly used for pretreatment compositions in textile printing, such as water, reduction inhibitors, preservatives, fungicides, chelating agents, pH adjusters, surfactants, viscosity modifiers, and antioxidants. Different from the foregoing ink jet ink for textile printing, corrosion inhibitors (including those having benzotriazole skeletons) may be contained.

The pretreatment composition may be attached to fabrics by the ink jet method. In such a case, the viscosity at 20° C. is preferably 1.5 mPa·s or more and 15 mPa·s or less, more preferably 1.5 mPa·s more and 5 mPa·s or less, and further preferably 1.5 mPa·s or more and 3.6 mPa·s or less.

Meanwhile, the pretreatment composition may be applied by methods other than the ink jet method. Exemplary such methods include either noncontact or contact methods and their combined methods, such as a method of applying a pretreatment composition by using various spraying devices, a method of applying a pretreatment composition through immersion of fabrics, and a method of applying a treatment solution to fabrics by using brushes or the like.

When the pretreatment composition is applied to fabrics by methods other than the ink jet method, the viscosity at 20° C. may be higher than the case by the ink jet method and is, for example, 1.5 mPa·s or more and 100 mPa·s or less, preferably 1.5 mPa·s or more and 50 mPa·s or less, and more preferably 1.5 mPa·s or more and 20 mPa·s or less. Here, the viscosity can be measured with a MCR-300 viscoelasticity tester (from Pysica) by increasing a shear rate from 10 to 1000 in an environment of 20° C. and reading the viscosity at a shear rate of 200.

3.3. Attaching Step

The textile printing method according to the embodiment includes a step of attaching the foregoing ink jet ink for textile printing to recording media, such as fabrics. Specifically, images are formed on recording media by attaching ink droplets discharged in an ink jet recording mode to the recording media. The ink jet recording mode may be any mode, and examples include a charging and deflecting mode, a continuous mode, and an on-demand mode [piezo mode, bubble jet (registered trademark) mode]. Among these ink jet recording modes, a mode using a piezo-type ink jet recording apparatus is particularly preferable.

3.4. Heat Treatment Step

The textile printing method according to the embodiment may include a step of heat-treating recording media to which the foregoing ink jet ink for textile printing has been attached. By performing a heat treatment step, fibers are dyed satisfactorily. The heat treatment step may employ conventionally known methods, and examples include a HT method (high-temperature steaming method), a HP method (high-pressure steaming method), and a thermosol method.

The temperature in the heat treatment step is preferably within the range of 90° or higher and 110° C. or lower from a viewpoint of suppressing damage on recording media.

3.5. Washing Step

The textile printing method according to the embodiment may include a step of washing printed articles.

The washing step is preferably performed after the above-described heat treatment step and can effectively remove dyes remaining without dyeing fibers. The washing step may be performed by using water, for example, and soaping treatment may be performed as necessary.

3.6. Other Steps

The textile printing method according to the embodiment may include, after the pretreatment step and before the attaching step, a step of drying a pretreatment composition that has been applied to a fabric. The pretreatment composition may be dried spontaneously but preferably involves heating from a viewpoint of increasing the drying rate. When the step of drying the pretreatment composition involves heating, the heating method is not particularly limited. Exemplary heating methods include a heat-pressing method, an atmospheric steaming method, a high-pressure steaming method, and a thermofixing method. Moreover, exemplary heating sources include, but are not limited to, infrared rays (lamps).

4. Examples and Comparative Examples

Hereinafter, present disclosure will be described in further detail with reference to the Examples. The present disclosure, however, is not limited to these Examples. Hereinafter, "part(s)", "%", and "ppm" are based on mass unless otherwise stated.

4.1. Preparation of Ink Jet Inks for Textile Printing

Ink jet inks for textile printing of Examples 1 to 19 and Comparative Examples 1 to 9 that are different in material composition were each prepared by feeding the respective components to a container so as to satisfy the composition shown in Tables 1 to 3, mixing and stirring by using a magnetic stirrer at ambient temperature for 1 hour, and filtering through a membrane filter with a pore size of 1 μm. The numerical values in Tables 1 to 3 represent % by mass, and deionized water was added so that the total mass of each ink reaches 100% by mass.

TABLE 1

| | | | Examples | | | | | | | | | |
|---|---|---|---|---|---|---|---|---|---|---|---|---|
| | | | 1 | 2 | 3 | 4 | 5 | 6 | 7 | 8 | 9 | 10 |
| Reactive dye | C.I.Reactive Black 8 | Bk | — | — | — | — | — | — | — | — | 0.30 | — |
| | C.I.Reactive Black 39 | | 0.30 | 0.30 | 0.30 | 0.30 | 0.30 | 0.30 | 0.70 | 0.20 | — | 0.30 |
| | C.I.Reactive Blue 13 | | — | — | — | — | — | — | — | — | — | — |
| | C.I.Reactive Blue 15:1 | | — | — | — | — | — | — | — | — | — | — |
| | C.I.Reactive Blue 49 | | 1.70 | 1.70 | 1.70 | 1.70 | 1.70 | 1.70 | 1.20 | 1.60 | 1.70 | 1.70 |
| | C.I.Reactive Yellow 95 | Or | — | — | — | — | — | — | — | — | — | — |
| | C.I.Reactive Orange 12 | | 0.10 | 0.10 | 0.10 | 0.10 | 0.10 | 0.10 | 0.15 | 0.10 | 0.10 | 0.10 |
| | C.I.Reactive Orange 13 | | — | — | — | — | — | — | — | — | — | — |
| | C.I.Reactive Orange 99 | | 0.40 | 0.40 | 0.40 | 0.40 | 0.40 | 0.40 | 0.30 | 0.35 | 0.40 | 0.40 |
| | C.I.Reactive Red 3:1 | R | — | — | — | — | — | — | — | 0.25 | — | — |
| | C.I.Reactive Red 245 | | 0.25 | 0.25 | — | — | — | — | 0.25 | — | 0.25 | 0.25 |
| | C.I.Reactive Red 24 | | — | — | 0.25 | — | — | — | — | — | — | — |
| | C.I.Reactive Red 24:1 | | — | — | — | 0.25 | — | — | — | — | — | — |
| | C.I.Reactive Red 226 | | — | — | — | — | 0.25 | — | — | — | — | — |
| | C.I.Reactive Red 31 | | — | — | — | — | — | 0.25 | — | — | — | — |
| Organic solvent | 2-pyrrolidone | | 5.00 | 5.00 | 5.00 | 5.00 | 5.00 | 5.00 | 5.00 | 5.00 | 5.00 | 5.00 |
| | Diethylene glycol monobutyl ether | | 5.00 | 5.00 | 5.00 | 5.00 | 5.00 | 5.00 | 5.00 | 5.00 | 5.00 | 5.00 |
| | Propylene glycol | | 22.0 | 22.0 | 22.0 | 22.0 | 22.0 | 22.0 | 22.0 | 22.0 | 22.0 | 22.0 |
| | Olfine PD002W (surfactant) | | 0.50 | 0.50 | 0.50 | 0.50 | 0.50 | 0.50 | 0.50 | 0.50 | 0.50 | 0.50 |
| | Tripropanolamine (pH adjuster) | | 0.20 | 0.20 | 0.20 | 0.20 | 0.20 | 0.20 | 0.20 | 0.20 | 0.20 | 0.20 |
| | Proxel XL-2 (preservative) | | 0.30 | 0.30 | 0.30 | 0.30 | 0.30 | 0.30 | 0.30 | 0.30 | 0.30 | 0.30 |
| | EDTA-2Na (chelating agent) | | — | 0.02 | — | — | — | — | — | — | 0.02 | 0.06 |
| | Benzotriazole (corrosion inhibitor) | | 0.01 | 0.01 | 0.01 | 0.01 | 0.01 | 0.01 | 0.01 | 0.01 | 0.01 | 0.01 |
| | Deionized water | | balance | balance | balance | balance | balance | balance | balance | balance | balance | balance |
| | Total (wt %) | | 100 | 100 | 100 | 100 | 100 | 100 | 100 | 100 | 100 | 100 |
| | Total reactive dyes (wt %) | | 2.75 | 2.75 | 2.75 | 2.75 | 2.75 | 2.75 | 2.60 | 2.50 | 2.75 | 2.79 |
| | Amount of Bk (wt %) | | 2.00 | 2.00 | 2.00 | 2.00 | 2.00 | 2.00 | 1.90 | 1.80 | 2.00 | 2.04 |
| | Amount of Bk/total (%) | | 72.7 | 72.7 | 72.7 | 72.7 | 72.7 | 72.7 | 73.0 | 72.0 | 72.7 | 73.1 |
| | Amount of Or (wt %) | | 0.50 | 0.50 | 0.50 | 0.50 | 0.50 | 0.50 | 0.45 | 0.45 | 0.50 | 0.50 |
| | Amount of Or/total (%) | | 18.2 | 18.2 | 18.2 | 18.2 | 18.2 | 18.2 | 17.3 | 18.0 | 18.2 | 17.9 |
| | Amount of R (wt %) | | 0.25 | 0.25 | 0.25 | 0.25 | 0.25 | 0.25 | 0.25 | 0.25 | 0.25 | 0.25 |
| | Amount of R/total (wt %) | | 9.16 | 9.16 | 9.16 | 9.16 | 9.09 | 9.09 | 9.68 | 10.0 | 9.09 | 9.02 |
| | RB49 (wt %) | | 1.70 | 1.70 | 1.70 | 1.70 | 1.70 | 1.70 | 1.20 | 1.60 | 1.70 | 1.70 |
| | RBk39/RB49 ratio (parts) | | 17.6 | 17.6 | 17.6 | 17.6 | 17.6 | 17.6 | 58.3 | 12.5 | 0.0 | 20.1 |
| | Or/RB49 ratio (parts) | | 29.4 | 29.4 | 29.4 | 29.4 | 29.4 | 29.4 | 37.5 | 28.1 | 29.4 | 29.4 |
| | R/RB49 ratio (parts) | | 14.8 | 14.8 | 14.8 | 14.8 | 14.7 | 14.7 | 21.0 | 15.6 | 14.7 | 14.8 |
| Evaluation results | 10 ppm or less of Ni, Co, and Cr | | A | A | A | A | A | A | A | A | B | A |
| | 500 ppm or less of EDTA | | A | A | A | A | A | A | A | A | A | B |
| | Hue and lightness of printed article | | A | A | A | A | A | A | A | A | A | A |
| | 1.0 or less of OD value (100% Duty) | | A | A | A | A | A | A | A | A | A | A |
| | Light resistance | OD | A | A | A | A | A | B | B | A | A | A |
| | Duty 100% | Discoloration | A | A | A | A | A | BB | BB | A | A | A |
| | Chlorine resistance | OD | A | A | A | A | A | C | A | A | B | A |
| | Duty 100% | Discoloration | A | A | A | A | A | C | A | A | B | A |
| | Environmental friendliness | | A | A | A | A | A | A | A | A | B | B |

TABLE 2

| | | | Examples | | | | | | | | |
|---|---|---|---|---|---|---|---|---|---|---|---|
| | | | 11 | 12 | 13 | 14 | 15 | 16 | 17 | 18 | 19 |
| Reactive dye | C.I.Reactive Black 8 | Bk | — | — | — | — | — | — | — | — | — |
| | C.I.Reactive Black 39 | | 0.30 | — | — | — | — | — | — | 0.30 | — |
| | C.I.Reactive Blue 13 | | — | — | — | — | — | — | — | — | — |
| | C.I.Reactive Blue 15:1 | | — | — | — | — | — | — | — | — | — |
| | C.I.Reactive Blue 49 | | 1.70 | 2.20 | 2.20 | 2.20 | 2.20 | 2.20 | 2.30 | 1.70 | 1.70 |
| | C.I.Reactive Yellow 95 | Or | — | — | — | 0.50 | — | — | — | — | — |
| | C.I.Reactive Orange 12 | | 0.10 | — | — | — | — | — | — | — | — |
| | C.I.Reactive Orange 13 | | — | — | — | — | — | — | — | — | — |
| | C.I.Reactive Orange 99 | | 0.40 | 0.45 | 0.50 | — | 0.40 | 0.70 | 0.45 | — | — |
| | C.I.Reactive Red 3:1 | R | — | — | 0.25 | 0.40 | 0.30 | 0.30 | — | — | — |
| | C.I.Reactive Red 245 | | — | 0.50 | — | — | — | — | 0.20 | — | — |
| | C.I.Reactive Red 24 | | — | — | — | — | — | — | — | — | — |
| | C.I.Reactive Red 24:1 | | — | — | — | — | — | — | — | — | — |
| | C.I.Reactive Red 226 | | — | — | — | — | — | — | — | — | — |
| | C.I.Reactive Red 31 | | 0.25 | — | — | — | — | — | — | — | — |
| Organic solvent | 2-pyrrolidone | | 5.00 | 5.00 | 5.00 | 5.00 | 5.00 | 5.00 | 5.00 | 5.00 | 5.00 |
| | Diethylene glycol monobutyl ether | | 5.00 | 5.00 | 5.00 | 5.00 | 5.00 | 5.00 | 5.00 | 5.00 | 5.00 |
| | Propylene glycol | | 22.0 | 22.0 | 22.0 | 22.0 | 22.0 | 22.0 | 22.0 | 22.0 | 22.0 |
| | Olfine PD002W (surfactant) | | 0.50 | 0.50 | 0.50 | 0.50 | 0.50 | 0.50 | 0.50 | 0.50 | 0.50 |
| | Tripropanolamine (pH adjuster) | | 0.20 | 0.20 | 0.20 | 0.20 | 0.20 | 0.20 | 0.20 | 0.20 | 0.20 |
| | Proxel XL-2 (preservative) | | 0.30 | 0.30 | 0.30 | 0.30 | 0.30 | 0.30 | 0.30 | 0.30 | 0.30 |
| | EDTA-2Na (chelating agent) | | 0.06 | 0.02 | 0.02 | 0.02 | 0.02 | 0.02 | 0.02 | — | — |
| | Benzotriazole (corrosion inhibitor) | | 0.01 | 0.01 | 0.01 | 0.01 | 0.01 | 0.01 | 0.01 | 0.01 | 0.01 |
| | Deionized water | | balance | balance | balance | balance | balance | balance | balance | balance | balance |
| | Total (wt %) | | 100 | 100 | 100 | 100 | 100 | 100 | 100 | 100 | 100 |
| | Total reactive dyes (wt %) | | 2.79 | 3.15 | 2.95 | 3.10 | 2.90 | 3.20 | 2.95 | 2.00 | 1.70 |
| | Amount of Bk (wt %) | | 2.04 | 2.20 | 2.20 | 2.20 | 2.20 | 2.20 | 2.30 | 2.00 | 1.70 |
| | Amount of Bk/total (%) | | 73.1 | 69.8 | 74.6 | 71.0 | 75.9 | 68.7 | 78 | 100 | 100 |
| | Amount of Or (wt %) | | 0.50 | 0.45 | 0.50 | 0.50 | 0.40 | 0.70 | 0.45 | 0.00 | 0.00 |
| | Amount of Or/total (%) | | 17.9 | 14.3 | 17.0 | 16.1 | 13.8 | 21.9 | 15.3 | 0.0 | 0.0 |
| | Amount of R (wt %) | | 0.25 | 0.50 | 0.25 | 0.40 | 0.30 | 0.30 | 0.20 | 0.00 | 0.00 |
| | Amount of R/total (%) | | 8.95 | 15.9 | 8.48 | 12.9 | 10.3 | 9.37 | 6.78 | 0.00 | 0.00 |
| | RB49 (wt %) | | 1.70 | 2.20 | 2.20 | 2.20 | 2.20 | 2.20 | 2.30 | 1.70 | 1.70 |
| | RBk39/RB49 ratio (parts) | | 20.1 | 0.0 | 0.0 | 0.0 | 0.0 | 0.0 | 0.0 | 17.6 | 0.0 |
| | Or/RB49 ratio (parts) | | 29.4 | 20.5 | 22.7 | 22.7 | 18.2 | 31.9 | 19.6 | 0.0 | 0.0 |
| | R/RB49 ratio (parts) | | 14.7 | 22.7 | 11.4 | 18.2 | 13.6 | 13.6 | 8.7 | 0.0 | 0.0 |
| Evaluation results | 10 ppm or less of Ni, Co, and Cr | | A | A | A | A | A | A | A | A | A |
| | 500 ppm or less of EDTA | | B | A | A | A | A | A | A | A | A |
| | Hue and lightness of printed article | | A | A | A | A | A | A | A | B | B |
| | 1.0 or less of OD value (100% Duty) | | A | A | A | A | A | A | A | A | A |
| | Light resistance OD | | B | A | A | A | A | A | A | A | A |
| | Duty 100% Discoloration | | BB | B | B | B | B | B | B | A | A |
| | Chlorine resistance OD | | C | B | A | A | B | B | B | C | D |
| | Duty 100% Discoloration | | C | B | A | A | B | B | B | C | D |
| | Environmental friendliness | | B | A | A | A | A | A | A | A | A |

TABLE 3

| | | | Comparative Examples | | | | | | | | |
|---|---|---|---|---|---|---|---|---|---|---|---|
| | | | 1 | 2 | 3 | 4 | 5 | 6 | 7 | 8 | 9 |
| Reactive dye | C.I.Reactive Black 8 | Bk | — | — | — | — | — | — | — | 1.50 | — |
| | C.I.Reactive Black 39 | | 0.40 | — | 0.30 | 0.30 | 0.80 | — | 1.60 | — | — |
| | C.I.Reactive Blue 13 | | — | — | — | — | — | — | — | — | — |
| | C.I.Reactive Blue 15:1 | | — | — | — | — | — | 1.60 | — | — | — |
| | C.I.Reactive Blue 49 | | 1.10 | 2.50 | 1.10 | 2.50 | — | 0.80 | — | — | 2.80 |
| | C.I.Reactive Yellow 95 | Or | — | — | — | — | 0.40 | — | — | — | — |
| | C.I.Reactive Orange 12 | | 0.10 | — | 0.10 | 0.10 | 0.20 | — | 0.40 | 0.20 | — |
| | C.I.Reactive Orange 13 | | — | — | — | — | — | — | 0.30 | — | 0.20 |
| | C.I.Reactive Orange 99 | | 0.30 | 0.40 | 0.40 | 0.40 | — | — | — | — | — |
| | C.I.Reactive Red 3:1 | R | 0.25 | — | — | — | 0.35 | 0.6 | 0.25 | 0.15 | — |
| | C.I.Reactive Red 245 | | — | 0.15 | 0.25 | 0.25 | — | — | — | — | — |
| | C.I.Reactive Red 24 | | — | — | — | — | — | — | — | — | — |
| | C.I.Reactive Red 24:1 | | — | — | — | — | — | — | — | — | — |
| | C.I.Reactive Red 226 | | — | — | — | — | — | — | — | — | — |
| | C.I.Reactive Red 31 | | — | — | — | — | — | — | — | — | — |
| Organic solvent | 2-pyrrolidone | | 5.00 | 5.00 | 5.00 | 5.00 | 5.00 | 5.00 | 5.00 | 5.00 | 5.00 |
| | Diethylene glycol monobutyl ether | | 5.00 | 5.00 | 5.00 | 5.00 | 5.00 | 5.00 | 5.00 | 5.00 | 5.00 |
| | Propylene glycol | | 22.0 | 22.0 | 22.0 | 22.0 | 22.0 | 22.0 | 22.0 | 22.0 | 22.0 |

TABLE 3-continued

|  |  | Comparative Examples | | | | | | | | |
|---|---|---|---|---|---|---|---|---|---|---|
|  |  | 1 | 2 | 3 | 4 | 5 | 6 | 7 | 8 | 9 |
|  | Olfine PD002W (surfactant) | 0.50 | 0.50 | 0.50 | 0.50 | 0.50 | 0.50 | 0.50 | 0.50 | 0.50 |
|  | Tripropanolamine (pH adjuster) | 0.20 | 0.20 | 0.20 | 0.20 | 0.20 | 0.20 | 0.20 | 0.20 | 0.20 |
|  | Proxel XL-2 (preservative) | 0.30 | 0.30 | 0.30 | 0.30 | 0.30 | 0.30 | 0.30 | 0.30 | 0.30 |
|  | EDTA-2Na (chelating agent) | — | 0.02 | — | — | 0.02 | 0.02 | 0.02 | 0.02 | 0.02 |
|  | Benzotriazole (corrosion inhibitor) | 0.01 | 0.01 | 0.01 | 0.01 | 0.01 | 0.01 | 0.01 | 0.01 | 0.01 |
|  | Deionized water | balance | balance | balance | balance | balance | balance | balance | balance | balance |
|  | Total (wt %) | 100 | 100 | 100 | 100 | 100 | 100 | 100 | 100 | 100 |
|  | Total reactive dyes (wt %) | 2.15 | 3.05 | 2.15 | 3.55 | 1.75 | 2.40 | 2.55 | 1.85 | 3.00 |
|  | Amount of Bk (wt %) | 1.50 | 2.50 | 1.40 | 2.80 | 0.80 | 1.60 | 1.60 | 1.50 | 2.80 |
|  | Amount of Bk/total (%) | 69.8 | 82.0 | 65.1 | 78.8 | 45.7 | 66.7 | 62.7 | 81.1 | 93.3 |
|  | Amount of Or (wt %) | 0.40 | 0.40 | 0.50 | 0.50 | 0.60 | 0.80 | 0.70 | 0.20 | 0.20 |
|  | Amount of Or/total (%) | 18.6 | 13.1 | 23.2 | 14.1 | 34.2 | 33.3 | 27.5 | 10.8 | 6.7 |
|  | Amount of R (wt %) | 0.25 | 0.15 | 0.25 | 0.25 | 0.35 | 0.00 | 0.25 | 0.15 | 0.00 |
|  | Amount of R/total (%) | 11.6 | 4.92 | 11.7 | 7.09 | 20.1 | 0.00 | 9.80 | 8.11 | 0.00 |
|  | RB49 (wt %) | 1.10 | 2.50 | 1.10 | 2.50 | 0.00 | 0.00 | 0.00 | 0.00 | 2.80 |
|  | RBk39/RB49 ratio (parts) | 36.4 | 0.0 | 27.3 | 12.0 | — | — | — | — | 0.0 |
|  | Or/RB49 ratio (parts) | 36.4 | 16.0 | 45.5 | 20.0 | — | — | — | — | 7.1 |
|  | R/RB49 ratio (parts) | 22.7 | 6.0 | 22.9 | 10.1 | — | — | — | — | 0.0 |
| Evaluation results | 10 ppm or less of Ni, Co, and Cr | A | A | A | A | A | A | A | B | A |
|  | 500 ppm or less of EDTA | A | A | A | A | A | A | A | A | A |
|  | Hue and lightness of printed article | A | A | A | A | A | A | A | A | B |
|  | 1.0 or less of OD value (100% Duty) | A | B | A | B | A | A | A | A | B |
| Light resistance Duty 100% | OD | C | A | C | A | D | D | D | D | D |
|  | Discoloration | BB | BB | BB | BB | C | C | C | C | C |
| Chlorine resistance Duty 100% | OD | C | C | C | B | D | D | D | D | D |
|  | Discoloration | C | C | C | C | D | D | D | D | D |
|  | Environmental friendliness | A | A | A | A | A | A | A | B | A |

In the tables, Olfine PD 002W is an acetylenic glycol surfactant from Nissin Chemical Industry Co. Ltd., and Proxel XL-2 is a preservative/fungicide from Lonza Japan Ltd.

The maximum absorption wavelength (nm) of each reactive dye and light absorbance (Abs./100 ppm) of each Bk and B dyes are as follows.

C.I. Reactive Black 8; 586 nm; 0.203
C.I. Reactive Black 39; 611 nm; 0.416
C.I. Reactive Blue 13; 568 nm; 0.211
C.I. Reactive Blue 15:1; 672 nm; 0.487
C.I. Reactive Blue 49; 587 nm; 0.174
C.I. Reactive Yellow 95; 422 nm
C.I. Reactive Orange 12; 420 nm
C.I. Reactive Orange 13; 488 nm
C.I. Reactive Orange 99; 421 nm
C.I. Reactive Red 3:1; 533 nm
C.I. Reactive Red 245; 543 nm
C.I. Reactive Red 24; 534 nm
C.I. Reactive Red 24:1; 534 nm
C.I. Reactive Red 226; 534 nm
C.I. Reactive Red 31; 535 nm Tables 1 to 3 also show, for the ink of each working example, the total amount (% by mass) of reactive dyes; the amount (% by mass) of Bk, Or, and R dyes and their ratio (%) relative to the total amount of the dyes; a ratio of C.I. Reactive Black 39 to RB 49 (parts by mass); a ratio of the total Or dyes to RB 49 (parts by mass); and a ratio of the total R dyes to RB 49 (parts by mass).

4.2. Evaluation Method
4.2.1. Evaluation of Inks
4.2 1. (1) Metal Content

Each ink was analyzed for Ni, Co, and Cr by using an ICP-MS (inductively coupled plasma-mass spectrometer). Each ink was evaluated as "A" when the total concentration of these elements is less than 10.0 ppm and as "B" when the total concentration is 10.0 ppm or more. The evaluation results are shown in Tables 1 to 3. The inks of Table 4 described hereinafter were also similarly evaluated, and the evaluation results are shown in Table 4.

4.2.1. (2) EDTA-2Na Content

According to the amount of EDTA-2Na fed to each ink, each ink is evaluated as "A" when the content of EDTA-2Na is 500.0 ppm (0.05% by mass) or less and as "B" when the content exceeds 500.0 ppm. The evaluation results are shown in Tables 1 to 3.

4.2.1. (3) Environmental Friendliness

Each ink is evaluated as environmental friendliness "A" when both evaluations for the above-mentioned metal content and EDTA-2Na content are A and as environmental friendliness "B" when either of the above-mentioned evaluations is B. The evaluation results are shown in Tables 1 to 3.

4.2.2. Evaluation of Printed Fabrics

Each of the above-described ink jet inks for textile printing was filled in a yellow cartridge of a PX-G930 ink jet printer (from Seiko Epson Corporation). Each fabric 1 (cotton 100%; basis weight of 130 g/m$^2$) treated with the pretreatment agent described hereinafter was set in the printer, and solid patterns were attached to the fabric while adjusting stepwise, from 5% duty to 100% duty, the amount of discharged ink. Here, the image resolution was set to 1440×720 dpi.

Preparation of Pretreatment Agent and Pretreatment Method for Fabrics

Five parts by mass of polyoxyethylene diisopropyl ether (oxyethylene=30 mol), 5 parts by mass of etherified carboxymethyl cellulose, 100 parts by mass of urea (hydrotropic agent), and 10 parts by mass of sodium m-nitrobenzenesulfonate were thoroughly mixed and then added in small portions to 1000 parts by mass of deionized water while stirring at 60° C. for 30 minutes. Subsequently, 30 parts by mass of sodium carbonate (alkaline agent) was further added to the solution being stirred, followed by stirring for 10 minutes. The resulting solution was filtered through a membrane filter with a pore size of 10 μm to yield a pretreatment agent. The obtained pretreatment agent was applied to fabric 1 (cotton 100%; basis weight of 130 g/m²) and dried by squeezing with a mangle at a pickup ratio of 80% to yield treated fabric 1.

Fabric 1 to which an ink jet ink for textile printing had been attached underwent steaming at 102° C. for 10 minutes. Subsequently, fabric 1 was washed with an aqueous solution containing 0.2% by mass of Laccol STA (surfactant from Meisei Chemical Works, Ltd.) at 90° C. for 10 minutes, followed by drying to yield a sample for evaluation.

4.2.2. (1) Evaluation of Printed Articles for Hue and Lightness

The L*, a*, b* values and OD value of an image in each obtained sample for evaluation were measured by using a spectrophotometer (trade name "FD-7" from Konica Minolta, Inc.) under conditions of light source: D65, status: T, viewing angle: 10°, and filter: D65. The sample is evaluated as "A" when a* is −20.0 or more and 0.0 or less, b* is −20.0 or more and 0.0 or less, and L* is 30.0 or more and 80.0 or less in the CIELAB color space and as "B" for other cases. The evaluation results are shown in Tables 1 to 3.

4.2.2. (2) Evaluation of Printed Articles for OD Values

The sample is evaluated as "A" when a value at 100% duty, among the OD values measured as above, is 1.0 or less and as "B" when the value exceeds 1.0. The evaluation results are shown in Tables 1 to 3. When a printed article is evaluated as A for the OD value, it is considered that the tone of a light ink is obtained and thus the effects of the present disclosure are obtained.

4.2.2. (3) Evaluation for Light Resistance

In evaluation for light resistance, a 100% duty portion of the printed fabric 1 (cotton: 100%, basis weight: 130 g/m²) was exposed for 10 days by using a Xenon weather meter (trade name "XL-75s" from Suga Test Instruments Co. Ltd.) under conditions of 23° C., relative humidity of 50% R.H., and illuminance of 75000 lux. Both the initial OD value and the OD value on day 10 were measured, and light resistance is evaluated on the basis of the OD residual ratio in accordance with the following criteria. The results are shown in Tables 1 to 3 as "OD" in the light resistance evaluation. Moreover, the color difference (ΔE*) between the initial and day 10 was calculated, and light resistance is evaluated in accordance with the following criteria. The results are shown in Tables 1 to 3 as "discoloration" in the light resistance evaluation. When the OD residual ratio is evaluated as B or better, the effects of the present disclosure are considered to be obtained.

OD Residual Ratio
A: 80% or more
B: 75% or more and less than 80%
C: 70% or more and less than 75%
D: less than 70%

Color Difference
A: ΔE* of less than 5
B: ΔE* of 5 or more and less than 7.5
BB: ΔE* of 7.5 or more and less than 10
C: ΔE* of 10 or more Here, the OD residual ratio (shown as "OD" in the tables) is calculated according to the following numerical expression 1:

$$\text{OD residual ratio (\%)}: OD_2 OD_1 \times 100 \quad (1)$$

where $OD_1$ represents the initial OD value of printed fabric 1, and $OD_2$ represents the OD value after the test (after 10 days).

Moreover, the color difference (ΔE*) is evaluated on the basis of the following numerical formulae 2 to 5:

$$\Delta E^* = [(\Delta L^*)^2 + (\Delta a^*)^2 + (\Delta b^*)^2]^{1/2} \quad (2)$$

$$\Delta L^* = L^*_1 - L^*_2 \quad (3)$$

$$\Delta a^* = a^*_1 - a^*_2 \quad (4)$$

$$\Delta b^* = b^*_1 - b^*_2 \quad (5)$$

where $L^*_1$, $a^*_1$, and $b^*_1$ represent initial L*, a*, and b* values of printed fabric 1, and $L^*_2$, $a^*_2$, and $b^*_2$ represent L*, a*, and b* values after the light resistance test (after 10 days).

4.2.2. (4) Evaluation for Chlorine Resistance

For chlorine resistance evaluation, the OD residual ratio and the color difference after immersing a 100% duty portion of the above-mentioned printed fabric 1 (cotton 100%: basis weight of 130 g/m²) in an aqueous solution of 200 ppm sodium hypochlorite at 25° C. for 30 minutes were evaluated. The results are shown in Tables 1 to 3 as "OD" and "discoloration" in the chlorine resistance evaluation.

OD Residual Ratio
A: 90% or more
B: 85% or more and less than 90%
C: 80% or more and less than 85%
D: less than 80%

Color Difference
A: ΔE* of less than 5
B: ΔE* of 5 or more and less than 7.5
C: ΔE* of 7.5 or more and less than 10
D: ΔE* of 10 or more Here, the OD residual ratio (shown as "OD" in the tables) and color difference (ΔE*) are evaluated on the basis of the OD value, and L*, a*, and b* values before and after the chlorine resistance test in the same manner as the light resistance test.

4.2.3. Evaluation of Ink Sets

Each black, cyan, magenta, yellow, blue, red, and orange ink jet ink for textile printing was prepared: by feeding the respective components to a container so as to satisfy the composition shown in Table 4; mixing and stirring by using a magnetic stirrer at ambient temperature for 1 hour; and filtering through a membrane filter with a pore size of 1 μm.

TABLE 4

| | | Black ink | Cyan ink | Magenta ink | Yellow ink | Blue ink | Red ink | Orange ink |
|---|---|---|---|---|---|---|---|---|
| Reactive dye | C.I.Reactive Black 39 | 10.00 | — | — | — | — | — | — |
| | C.I.Reactive Blue 15:1 | — | 10.00 | — | — | — | — | — |
| | C.I.Reactive Blue 49 | — | — | — | — | 10.00 | — | — |
| | C.I.Reactive Yellow 95 + | — | — | — | 10.00 | — | — | — |

TABLE 4-continued

|  |  | Black ink | Cyan ink | Magenta ink | Yellow ink | Blue ink | Red ink | Orange ink |
|---|---|---|---|---|---|---|---|---|
|  | C.I.Reactive Yellow 2 |  |  |  |  |  |  |  |
|  | C.I.Reactive C.I. Orange 12 | 2.50 | — | — | — | — | — | — |
|  | C.I.Reactive Orange 13 | 1.50 | — | — | — | — | — | 10.00 |
|  | C.I.Reactive Red 3:1 | 1.50 | — | — | — | — | 10.00 | — |
|  | C.I.Reactive Red 31 | — | — | 10.00 | — | — | — | — |
| Organic solvent | 2-Pyrrolidone | 5.00 | 5.00 | 5.00 | 5.00 | 5.00 | 5.00 | 5.00 |
|  | Diethylene glycol monobutyl ether | 5.00 | 5.00 | 5.00 | 5.00 | 5.00 | 5.00 | 5.00 |
|  | Propylene glycol | 10.0 | 10.0 | 10.0 | 10.0 | 10.0 | 10.0 | 10.0 |
|  | Olfine PD002W (surfactant) | 0.50 | 0.50 | 0.50 | 0.50 | 0.50 | 0.50 | 0.50 |
|  | Tripropanolamine (pH adjuster) | 0.20 | 0.20 | 0.20 | 0.20 | 0.20 | 0.20 | 0.20 |
|  | Proxel XL-2 (preservative) | 0.30 | 0.30 | 0.30 | 0.30 | 0.30 | 0.30 | 0.30 |
|  | EDTA-2Na (chelating agent) | 0.02 | 0.02 | 0.02 | 0.02 | 0.02 | 0.02 | 0.02 |
|  | Benzotriazole (corrosion inhibitor) | 0.01 | 0.01 | 0.01 | 0.01 | 0.01 | 0.01 | 0.01 |
| Water | Deionized water | balance | balance | balance | balance | balance | balance | balance |
|  | Total (wt %) | 100 | 100 | 100 | 100 | 100 | 100 | 100 |
|  | 10 ppm or less of Ni, Co, and Cr | A | A | A | A | A | A | A |

An ink jet ink set for textile printing was prepared by combining with the respective ink jet inks for textile printing in Example 1. The cartridges of a modified PX-G930 ink jet printer (from Seiko Epson Corporation) were filled with the respective inks, and all the inks were discharged. Satisfactory dischargeability and satisfactory light resistance evaluation of formed images were confirmed. Moreover, any of the inks does not use metal-containing dyes. Each ink was measured in the same manner as in the above-described "4.2.1. (1) Metal Content". Consequently, the total concentration of Ni, Co, and Cr was less than 10.0 ppm for all the inks.

4.3. Evaluation Results

As shown in Tables 1 to 3, all the ink jet inks for textile printing of the Examples, in which C.I. Reactive Blue 49 (RB 49) is contained in 1.2% by mass or more and 2.3% by mass or less relative to the total amount of each ink, exhibit satisfactory optical density (OD) and excellent light resistance (OD residual ratio) of printed articles.

In contrast, the ink jet inks for textile printing of the respective Comparative Examples, in which RB 49 is contained in less than 1.2% by mass or in 2.3% by mass or more relative to the total amount of each ink, exhibit either unsatisfactory optical density (OD) or light resistance (OD residual ratio) of printed articles or both.

The present disclosure is not limited to the above-described embodiments, and various modifications are possible. For example, the present disclosure encompasses the constitution substantially the same as the constitution described in the embodiments (constitution with the same function, method, and results; or constitution with the same object and effects, for example). In addition, the present disclosure encompasses the constitution in which a nonessential portion of the constitution described in the embodiments is replaced. Moreover, the present disclosure encompasses the constitution that exerts the same effects as the constitution described in the embodiments or the constitution that can attain the same object as the constitution described in the embodiments. Further, the present disclosure encompasses the constitution in which a publicly known technique is added to the constitution described in the embodiments.

What is claimed is:

1. An ink jet ink for textile printing, comprising:

a reactive dye; and

C.I. Reactive Black 39, wherein 1.2% by mass or more and 2.3% by mass or less of C.I. Reactive Blue 49 based on a total amount of the ink is contained as the reactive dye; and wherein a content of the C.I. Reactive 39 is 10.0 parts by mass or more and 25.0 parts by mass or less relative to 100 parts by mass of the C.I. Reactive Blue 49 contained.

2. The ink jet ink for textile printing according to claim 1, wherein a total content of nickel ions, cobalt ions, and chromium ions in the ink is 10.0 ppm or less based on the total amount of the ink.

3. The ink jet ink for textile printing according to claim 1, further comprising:

a reactive dye having a maximum absorption wavelength of 500.0 nm or more and less than 550.0 nm; and a reactive dye having a maximum absorption wavelength of 400.0 nm or more and less than 500.0 nm.

4. The ink jet ink for textile printing according to claim 3, wherein a content of the reactive dye having a maximum absorption wavelength of 400.0 nm or more and less than 500.0 nm is 20.0 parts by mass or more and 30.0 parts by mass or less relative to 100 parts by mass of C.I. Reactive Blue 49 contained.

5. The ink jet ink for textile printing according to claim 3, wherein a content of the reactive dye having a maximum absorption wavelength of 500.0 nm or more and less than 550.0 nm is 10.0 parts by mass or more and 20.0 parts by mass or less relative to 100 parts by mass of C.I. Reactive Blue 49 contained.

6. The ink jet ink for textile printing according to claim 3, wherein the reactive dye having a maximum absorption wavelength of 400.0 nm or more and less than 500.0 nm has a structure represented by the following formula (I):

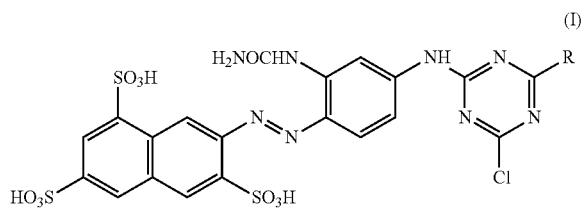

(I)

wherein R represents —NHCH$_2$CH$_2$SO$_3$H, —NH$_2$, or —CH$_2$CH$_2$OCH$_2$CH$_2$OH.

7. The ink jet ink for textile printing according to claim 3, wherein the reactive dye having a maximum absorption wavelength of 500.0 nm or more and less than 550.0 nm has a structure represented by the following formula (II):

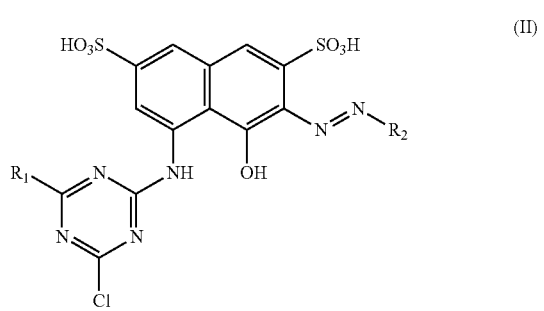

(II)

wherein R$^1$ is selected from groups represented by the following formula (III), formula (IV), formula (V), and formula (VI) (in each formula, a position represented by a dashed line is a connection point); and R$^2$ is selected from groups represented by the following formula (VII) and formula (VIII) (in each formula, a position represented by a dashed line is a connection point).

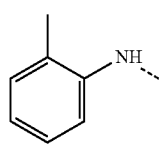

(III)

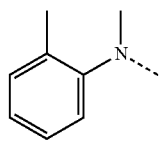

(IV)

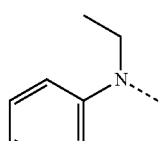

(V)

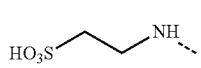

(VI)

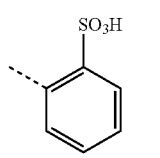

(VII)

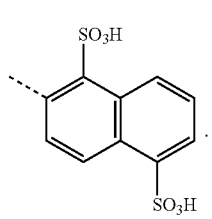

(VIII)

8. The ink jet ink for textile printing according to claim 1, wherein when a fabric is printed with the ink, a* is −20.0 or more and 0.0 or less, b* is −20.0 or more and 0.0 or less, and L* is 30.0 or more and 80.0 or less.

9. The ink jet ink for textile printing according to claim 1, further comprising a chelating agent, wherein a content of the chelating agent is 500.0 ppm or less based on the total amount of the ink.

10. An ink set comprising the ink jet ink for textile printing according to claim 1.

11. The ink set according to claim 10, wherein all inks included in the ink set have a total content of nickel ions, cobalt ions, and chromium ions of 10.0 ppm or less based on a total amount of each ink.

12. A textile printing method comprising attaching the ink jet ink for textile printing according to claim 1 to a recording medium.

\* \* \* \* \*